US012576752B2

(12) United States Patent
Kim et al.

(10) Patent No.: US 12,576,752 B2
(45) Date of Patent: Mar. 17, 2026

(54) VEHICLE SEAT CONTROL APPARATUS AND METHOD THEREOF

(71) Applicants: HYUNDAI MOTOR COMPANY, Seoul (KR); KIA CORPORATION, Seoul (KR)

(72) Inventors: Ki Chang Kim, Suwon-si (KR); Dong Chul Park, Anyang-si (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 177 days.

(21) Appl. No.: 18/380,499

(22) Filed: Oct. 16, 2023

(65) Prior Publication Data

US 2024/0317114 A1 Sep. 26, 2024

(30) Foreign Application Priority Data

Mar. 24, 2023 (KR) ........................ 10-2023-0038841

(51) Int. Cl.
*B60N 2/00* (2006.01)
*A61M 21/00* (2006.01)
(Continued)

(52) U.S. Cl.
CPC ........... *B60N 2/0023* (2023.08); *A61M 21/02* (2013.01); *B60N 2/90* (2018.02);
(Continued)

(58) Field of Classification Search
CPC .. B60N 2/0023; B60N 2/90; B60N 2002/981; A61M 21/02; A61M 2021/0022;
(Continued)

(56) References Cited

U.S. PATENT DOCUMENTS 11,369,771 B2     6/2022  Lazarovich
11,710,472 B2 *   7/2023  Farahanisamani ...........................
                                        G10K 11/17825
                                        381/71.4
(Continued)

FOREIGN PATENT DOCUMENTS

CN      205168252 U   *  4/2016
JP      2017504376 A  *  2/2017   ......... A61B 5/02438
(Continued)

OTHER PUBLICATIONS

Hasegawa et al, Affective Vibrotactile Stimuli, 2019, International Journal of Affective Engineering vol. 18 No. 4 pp. 171-180 (Year: 2019).*
(Continued)

*Primary Examiner* — Hitesh Patel
*Assistant Examiner* — Austin Robert Chennault
(74) *Attorney, Agent, or Firm* — Lempia Summerfield Katz LLC

(57) ABSTRACT

A vehicle seat control apparatus for controlling seat vibration based on a sleep state of a driver and a method thereof are provided. The apparatus includes a detector that detects biometric information of a user and a driving device that controls a vibrator embedded in a vehicle seat. The apparatus further includes a controller connected with the detector and the driving device. The controller determines a sleep state of the user based on the biometric information detected by the detector, determines a frequency and a waveform of seat vibration based on the sleep state, and generates the seat vibration by controlling the driving device based on the frequency and the waveform of the seat vibration.

29 Claims, 5 Drawing Sheets

(51) Int. Cl.
    *A61M 21/02*           (2006.01)
    *B60N 2/90*            (2018.01)

(52) U.S. Cl.
    CPC .............. *A61M 2021/0022* (2013.01); *A61M 2021/0027* (2013.01); *A61M 2205/3306* (2013.01); *A61M 2230/10* (2013.01); *A61M 2230/62* (2013.01); *B60N 2002/981* (2018.02)

(58) Field of Classification Search
    CPC .. A61M 2021/0027; A61M 2205/3306; A61M 2230/10; A61M 2230/62; A61M 21/00
    USPC .......................................................... 701/49
    See application file for complete search history.

(56) References Cited

U.S. PATENT DOCUMENTS

| | | | | |
|---|---|---|---|---|
| 2012/0223900 A1* | 9/2012 | Jiyama | ................ | G06F 3/04142 |
| | | | | 345/173 |
| 2018/0281627 A1* | 10/2018 | Ali | ........................ | B60N 2/0022 |
| 2019/0299830 A1* | 10/2019 | Alequin | .................... | B60N 2/56 |

| | | | | | |
|---|---|---|---|---|---|
| 2020/0219615 A1* | 7/2020 | Rabin | .................... | | G16H 20/00 |
| 2020/0331501 A1 | 10/2020 | Wirtz | | | |
| 2021/0101512 A1* | 4/2021 | Shimizu | ................... | | B60Q 9/00 |
| 2021/0401184 A1* | 12/2021 | Manwaring | ........... | | A61M 21/02 |
| 2022/0340225 A1* | 10/2022 | Iizuka | .................... | | B62J 50/225 |

FOREIGN PATENT DOCUMENTS

| | | | | | | |
|---|---|---|---|---|---|---|
| JP | 2018052358 A | * | 4/2018 | | | |
| JP | 2020056932 A | | 4/2020 | | | |
| JP | 6933467 B2 | | 9/2021 | | | |
| JP | 2022104022 A | | 7/2022 | | | |
| KR | 20060107648 A | | 10/2006 | | | |
| KR | 20180009409 A | | 1/2018 | | | |
| KR | 20220146849 A | | 11/2022 | | | |
| WO | WO-2014007011 A1 | * | 1/2014 | ............. | | B60N 2/502 |

OTHER PUBLICATIONS

Han-Kee Jang; Human Vibration in Vehicle Development; Journal of the Korean Society of Automotive Engineers; vol. 23(2), 2001, pp. 72-78.

* cited by examiner

DETERMINE SLEEP STATE S210

MEASURE WEIGHT OF USER S220

DETERMINE VIBRATION FREQUENCY AND VIBRATION WAVEFORM OF BACK AND THIGHS S230

CORRECT VIBRATION EXCITING FORCE IN X DIRECTION AND Z DIRECTION BASED ON SITTING POSTURE S240

OCCURRENCE OF VIBRATION S250

MEASURE EEG AND HEART RATE S260

DOES THRESHOLD TIME ELAPSE AFTER CHANGE IN SLEEP STATE? S270

NO

YES

VEHICLE SEAT CONTROL APPARATUS AND METHOD THEREOF

CROSS-REFERENCE TO RELATED APPLICATION

This application claims the benefit of and priority to Korean Patent Application No. 10-2023-0038841, filed in the Korean Intellectual Property Office on Mar. 24, 2023, the entire contents of which are incorporated herein by reference.

TECHNICAL FIELD

The present disclosure relates to a vehicle seat control apparatus for controlling seat vibration based on a sleep state of a driver and a method thereof.

BACKGROUND

Various technologies are utilized in autonomous vehicles to provide comfort in the autonomous vehicles as well as improve safety and driving performance of the autonomous vehicles. As an example, a motion seat may apply a plurality of air pockets to the inside of a vehicle seat and may separately control the plurality of air pockets, thus providing an optimal driving posture and reducing fatigue through a comfortable sense of sitting. As another example, a lighting system may be utilized to help a child riding in the rear seat of the vehicle to sleep. As yet another example, a massage function may be applied to the vehicle seat to reduce fatigue of the driver.

SUMMARY

The present disclosure has been made to solve the above-mentioned problems occurring in the prior art while advantages achieved by the prior art are maintained intact.

An aspect of the present disclosure provides a vehicle seat control apparatus for monitoring a sleep state of a user using electroencephalogram (EEG) and controlling seat vibration based on the sleep state, and a method thereof.

Another aspect of the present disclosure provides a vehicle seat control apparatus for dividing a sleep state into three stages and controlling a seat vibration pattern through a customized frequency change for each divided stage, and a method thereof.

The technical problems to be solved by the present disclosure are not limited to the aforementioned problems. Other technical problems not mentioned herein should be clearly understood from the following description by those having ordinary skill in the art to which the present disclosure pertains.

According to an aspect of the present disclosure, a vehicle seat control apparatus is provided. The apparatus may include a detector configured to detect biometric information of a user. The apparatus may also include a driving device configured to control a vibrator embedded in a vehicle seat. The apparatus may further include a controller connected with the detector and the driving device. The controller may be configured to determine a sleep state of the user based on the biometric information detected by the detector. The controller may also be configured to determine a frequency and a waveform of seat vibration based on the sleep state. The controller may further be configured to generate the seat vibration by controlling the driving device based on the frequency and the waveform of the seat vibration.

The detector may include an electroencephalogram (EEG) measurement device that measures an EEG of the user.

The controller may be configured to analyze the EEG of the user and determines the sleep state based on a result of analyzing the EEG.

The sleep state may be divided into a sleep boundary stage, a sleep stage, and a deep sleep stage.

The controller may be configured to select the waveform of the seat vibration as a sine wave in response to determining that the sleep state is the sleep boundary stage. The controller may further be configured to select the waveform of the seat vibration as a crossing wave in which a sine wave and a triangle wave cross with each other in response to determining that the sleep state is the sleep stage. The controller may additionally be configured to select the waveform of the seat vibration as a triangle wave in response to determining that the sleep state is the deep sleep stage.

The controller may be configured to select a frequency of the seat vibration based on the sleep state.

The controller may be configured to set a concept of correlation between sleep and frequency by analyzing vibration frequency distribution and a ratio of sleeping passengers. The controller may further be configured to set a vibration mode map capable of avoiding resonance between a natural frequency of a vehicle and a natural frequency of a human body based on the set concept. The controller may additionally be configured to select a frequency capable of avoiding resonance between the vehicle and the human body as the frequency of the seat vibration with reference to the vibration mode map.

The controller may be configured to determine a frequency of the seat vibration, the frequency of the seat vibration corresponding to the sleep state, based on a weight of the user.

The controller may be configured to determine a seat back vibration frequency and a seat cushion vibration frequency with regard to weight distribution for each body part through an analysis of human modeling-based big data according to a sitting state.

The detector may be configured to detect frequency-acceleration and surface pressure for each seat portion using a pressure sensor.

The controller may be configured to analyze whether a body part is close to the vehicle seat, surface pressure distribution, and a load balance based on the frequency-acceleration and the surface pressure for each seat portion and may determine a sitting posture of the user based on the analyzed result.

The controller may be configured to correct a vibration excitation force based on the sitting posture of the user.

The controller may be configured to decrease a frequency amplitude of a portion where the vibration excitation force is high based on pressure applied to the vehicle seat and may increase a frequency amplitude of a portion where the vibration excitation force is low.

The controller may be configured to monitor the sleep state of the user based on the biometric information detected by the detector while generating the seat vibration and may recognize a change in the sleep state based on the result of monitoring the sleep state of the user.

The controller may be configured to redetermine a frequency and a waveform of the seat vibration in response to detecting that a predetermined threshold time elapses after the change in the sleep state is recognized.

The controller may be configured to monitor the sleep state of the user using a camera and may adjust an angle of at least one of the vehicle seat, a leg support, or a combination thereof based on the result of monitoring the sleep state of the user.

The controller may be configured to measure interior noise of a vehicle using a noise measurement device and may control an operation of a noise canceling function based on the measured interior noise.

According to another aspect of the present disclosure, a vehicle seat control method is provided. The vehicle seat control method may include detecting biometric information of a user using a detector. The vehicle seat control method may also include determining a sleep state of the user based on the biometric information. The vehicle seat control method may further include determining a frequency and a waveform of seat vibration based on the sleep state. The vehicle seat control method may additionally include generating the seat vibration by controlling a driving device based on the frequency and the waveform of the seat vibration.

Detecting the biometric information of the user may include measuring an EEG of the user using an EEG measurement device.

Determining the sleep state of the user may include analyzing the EEG of the user and determining the sleep state based on a result of analyzing the EEG.

The sleep state may be divided into a sleep boundary stage, a sleep stage, and a deep sleep stage.

Determining the frequency and the waveform of the seat vibration may include selecting the waveform of the seat vibration as a sine wave in response to determining that the sleep state is the sleep boundary stage. Determining the frequency and the waveform of the seat vibration may also include selecting the waveform of the seat vibration as a crossing wave in which a sine wave and a triangle wave cross with each other in response to determining that the sleep state is the sleep stage. Determining the frequency and the waveform of the seat vibration may additionally include selecting the waveform of the seat vibration as a triangle wave in response to determining that the sleep state is the deep sleep stage.

Determining the frequency and the waveform of the seat vibration may include selecting a frequency of the seat vibration based on the sleep state.

Selecting the frequency of the seat vibration may include setting a concept of correlation between sleep and frequency by analyzing vibration frequency distribution and a ratio of sleeping passengers. Selecting the frequency of the seat vibration may also include setting a vibration mode map capable of avoiding resonance between a natural frequency of a vehicle and a natural frequency of a human body based on the set concept. Selecting the frequency of the seat vibration may additionally include selecting a frequency capable of avoiding resonance between the vehicle and the human body as the frequency of the seat vibration with reference to the vibration mode map.

Determining the frequency and the waveform of the seat vibration may include measuring a weight of the user and determining a frequency of the seat vibration, the frequency of the seat vibration corresponding to the sleep state, based on the weight of the user.

Determining the frequency and the waveform of the seat vibration may include determining a seat back vibration frequency and a seat cushion vibration frequency with regard to weight distribution for each body part through an analysis of human modeling-based big data according to a sitting state.

The vehicle seat control method may further include determining a sitting posture of the user and correcting a vibration excitation force based on the sitting posture.

Determining the sitting posture of the user may include determining frequency-acceleration and surface pressure for each seat portion using a pressure sensor. Determining the sitting posture of the user may also include analyzing whether a body part is close to a vehicle seat, surface pressure distribution, and a load balance based on the frequency-acceleration and the surface pressure for each seat portion. Determining the sitting posture of the user may additionally include determining the sitting posture based on the analyzed result.

The vehicle seat control method may further include correcting a vibration excitation force based on the sitting posture of the user, after determining the sitting posture of the user.

Correcting the vibration excitation force may include decreasing a frequency amplitude of a portion where the vibration excitation force is high based on pressure applied to the vehicle seat and increasing a frequency amplitude of a portion where the vibration excitation force is low.

The vehicle seat control method may further include monitoring the sleep state of the user based on the biometric information detected by the detector while generating the seat vibration. The vehicle seat control method may further still include recognizing a change in the sleep state based on the result of monitoring the sleep state of the user. The vehicle seat control method may further include redetermining a frequency and a waveform of the seat vibration in response to detecting that a predetermined threshold time elapses after the change in the sleep state is recognized.

The vehicle seat control method may further include monitoring the sleep state of the user using a camera and adjusting an angle of at least one of a vehicle seat, a leg support, or a combination thereof based on the result of monitoring the sleep state of the user.

The vehicle seat control method may further include measuring interior noise of a vehicle using a noise measurement device and controlling an operation of a noise canceling function based on the measured interior noise.

BRIEF DESCRIPTION OF THE DRAWINGS

The above and other objects, features and advantages of the present disclosure should be more apparent from the following detailed description taken in conjunction with the accompanying drawings, in which.

DETAILED DESCRIPTION

Figure 1:
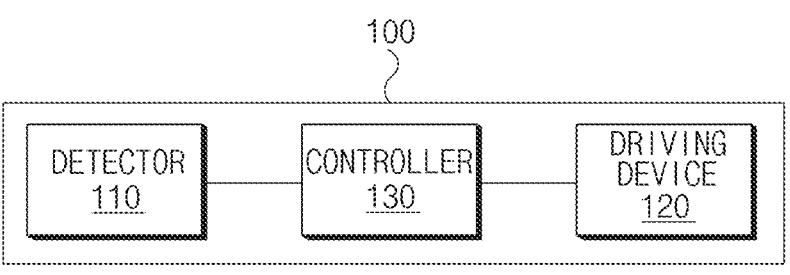
FIG. 1 is a block diagram illustrating a configuration of a vehicle seat control apparatus, according to embodiments of the present disclosure.

Hereinafter, embodiments of the present disclosure are described in detail with reference to the accompanying drawings. In the accompanying drawings, the same reference numerals are used throughout to designate the same or equivalent elements. Further, in the following description, a detailed description of a well-known feature or function has been omitted in order not to unnecessarily obscure the gist of the present disclosure. When a component, device, element, or the like of the present disclosure is described as having a purpose or performing an operation, function, or the like, the component, device, or element should be considered herein as being "configured to" meet that purpose or perform that operation or function.

In describing the components of the embodiment according to the present disclosure, terms such as first, second, "A", "B", (a), (b), and the like may be used. These terms are only used to distinguish one element from another element. These terms do not limit the nature, order, sequence, or priority of the elements. Furthermore, unless otherwise defined, all terms including technical and scientific terms used herein should be interpreted as is customary in the art to which the present disclosure puritans. Terms used herein should be interpreted as having a meaning that is consistent with their meaning in the context of the present disclosure and the relevant art and should not be interpreted in an idealized or overly formal sense unless expressly so defined herein.

Figure 2:
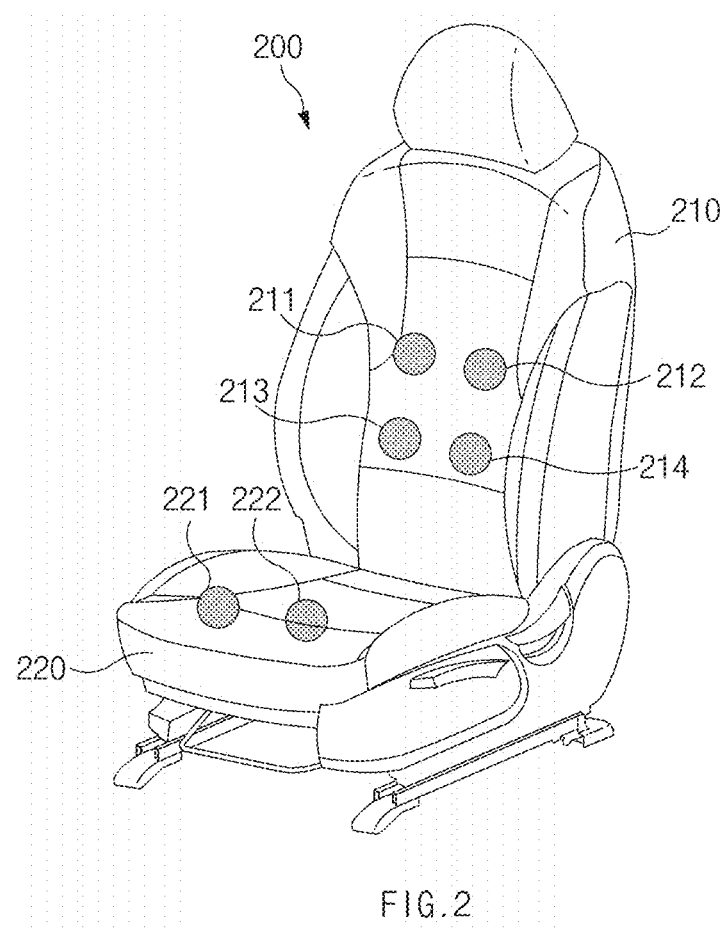
FIG. 2 is a drawing illustrating an example of installing vibrators, according to embodiments of the present disclosure.
Figure 3:
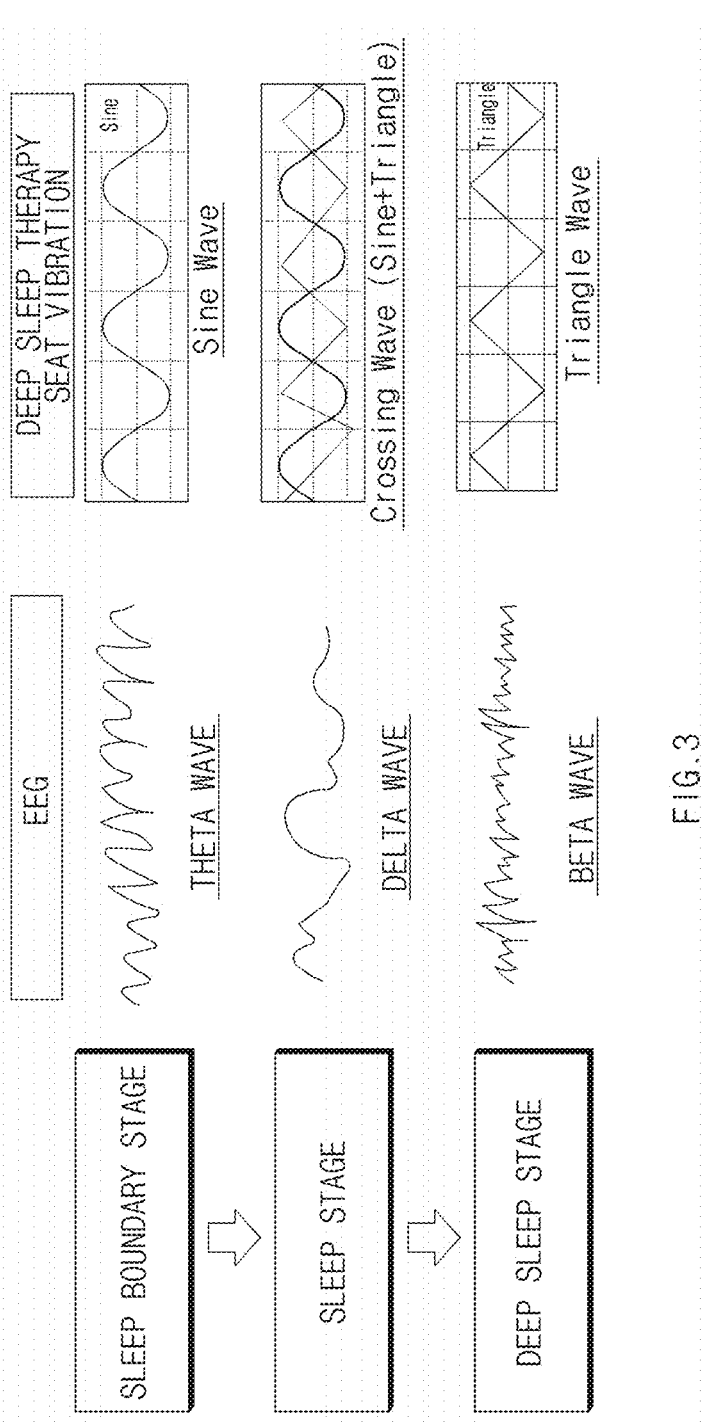
FIG. 3 is a drawing illustrating a seat vibration pattern according to a sleep state, according to embodiments of the present disclosure.

FIG. 1 is a block diagram illustrating a configuration of a vehicle seat control apparatus, according to embodiments of the present disclosure. FIG. 2 is a drawing illustrating an example of installing vibrators, according to embodiments of the present disclosure. FIG. 3 is a drawing illustrating a seat vibration pattern according to a sleep state, according to embodiments of the present disclosure.

Referring to FIG. 1, a vehicle seat control apparatus 100 may include a detector 110, a driving device 120, and a controller 130.

The detector 110 may obtain biometric information about a user (e.g., a driver, a passenger, and/or the like) sitting on a vehicle seat. The biometric information may include an electroencephalogram (EEG), a heart rate, and/or the like. The detector 110 may measure an EEG of the user using a contact EEG measurement device. The detector 110 may measure a heart rate of the user using a non-contact electrocardiography (ECG) measurement device embedded in the vehicle seat. The non-contact ECG measurement device may measure ECG by detecting an electric field generated by a heartbeat using a plurality of electric field sensors embedded in the vehicle seat.

The detector 110 may detect a weight and/or a sitting posture of the user using a sensor embedded in the vehicle seat. The detector 110 may measure a weight of the user using a weight measurement element (or a weight sensor) embedded in the vehicle seat. The detector 110 may measure surface pressure for each seat portion (e.g., a seat back, a seat cushion, a leg-rest, and/or the like) of a plurality of seat positions of the vehicle seat using a pressure sensor embedded in the vehicle seat. The pressure sensor may be mounted for each seat portion of the plurality of seat positions of the vehicle seat. For example, two pressure sensors may be mounted on the seat back, and two pressure sensors may be mounted on the seat cushion. The detector 110 may measure frequency-acceleration using an accelerometer embedded in the vehicle seat.

The driving device 120 may separately control a plurality of vibrators installed in the vehicle seat. Referring to FIG. 2, the plurality of vibrators may be mounted on a seat back 210 and a seat cushion 220 of a vehicle seat 200. As an example, four vibrators 211-214 may be installed in the seat back 210, and two vibrators 221 and 222 may be installed in the seat cushion 220.

The driving device 120 may control the plurality of vibrators 211-214, 221, and 222 under an instruction of the controller 130 to generate seat vibration. The driving device 120 may receive information including a vibration frequency, a vibration waveform, and/or the like from the controller 130. The driving device 120 may control excitation of the plurality of vibrators 211-214, 221, and 222 based on the received vibration frequency, the received vibration waveform, and/or the like to generate seat vibration.

The controller 130 may be connected with the detector 110 and the driving device 120 to transmit and receive data and/or control signals (e.g., control commands) therebetween. The controller 130 may control the overall operation of the vehicle seat control apparatus 100.

The detector 110, the driving device 120, and the controller 130 may include, or may be implemented on, at least one processor. The at least one processor may be implemented as an application specific integrated circuit (ASIC), a digital signal processor (DSP), programmable logic devices (PLD), field programmable gate arrays (FPGA), a central processing unit (CPU), microcontrollers, microprocessors, and/or the like.

The detector 110, the driving device 120, and/or the controller 130 may include a memory inside and/or outside. The memory may be a non-transitory storage medium which stores instructions executed by the at least one processor. The memory may be implemented as a flash memory, a hard disk, a solid state disk (SSD), a secure digital (SD) card, a random access memory (RAM), a static RAM (SRAM), a read only memory (ROM), a programmable ROM (PROM), an electrically erasable and programmable ROM (EEPROM), an erasable and programmable ROM (EPROM), and/or the like.

The controller 130 may receive sleep state information transmitted from a user interface (e.g., a touch screen, a button, and/or the like). For example, when a user selects a sleep state by means of a user interface (not shown), the controller 130 may determine the sleep state based on sleep state selection information transmitted from the user interface (not shown). The sleep state may be divided into a sleep boundary stage, a sleep stage, and a deep sleep stage. The sleep boundary stage may refer to a boundary between being awake and falling asleep. The sleep stage may refer to a stabilized state while breathing and a heart rate are lowered. The deep sleep stage may refer to a rapid eye movement (REM) sleep stage.

The controller 130 may monitor an EEG of the user by means of the detector 110. The controller 130 may analyze a pattern of the EEG measured by the detector 110 and may determine a sleep state of the user. When the detected EEG is a theta wave, the controller 130 may determine the sleep state as the sleep boundary stage. When the detected EEG is a delta wave, the controller 130 may determine the sleep state as the sleep stage. When the detected EEG is a beta wave, the controller 130 may determine the sleep state as the deep sleep stage.

The controller 130 may analyze frequency-acceleration and/or surface pressure for each seat portion detected by the detector 110 and may determine a weight and a sitting posture (or a sitting state) of the user sitting on the vehicle seat. The controller 130 may analyze whether a body part is close to the seat back based on frequency-acceleration in the seat back and a load balance (or a left and right direction Y and a forward and backward direction X) based on frequency-acceleration in the seat cushion and may determine (or estimate) a sitting posture (or a surface pressure distribution area). The controller 130 may determine whether a body part (e.g., a back or thighs) of the user is close to the seat back based on the frequency-acceleration in the seat back. The controller 130 may analyze a surface pressure distribution of the seat back and a lower frame, a surface pressure distribution of the seat cushion, and/or the like and may determine a load balance (or weight distribution) on the vehicle seat.

When the sleep state is determined, the controller 130 may determine a vibration frequency and a vibration waveform of the vehicle seat based on the determined sleep state. The controller 130 may control the driving device 120 based on the determined vibration frequency and the determined vibration waveform to generate vibration (or a vibration signal) on the vehicle seat.

The controller 130 may select an appropriate frequency based on the sleep state. The appropriate frequency according to the sleep state may be implemented by the following procedure. The controller 130 may set a concept of correlation between sleep and frequency. The controller 130 may set the concept of correlation between sleep and frequency based on the result of analyzing vibration frequency distribution and a ratio of sleeping passengers (RSP). As an example, the controller 130 may set a concept using a vibration frequency which may be low-frequency vibration excitation of 10 Hz or more and may continuously assign monotonous vibration pattern stimulation for a period of time (e.g., a relatively long period of time).

The controller 130 may be configured to avoid resonance between a natural frequency of a vehicle and a natural frequency of a human body based on the set concept. Because regular vibration of a low frequency of 4 Hz to 7 Hz delivered through the vehicle seat may be a cause of drowsy driving, this frequency may be considered as a valid frequency for sleep and/or deep sleep. Furthermore, when the vehicle and the human body resonate, because the amplitude increases to cause motion sickness, it may be required to set a vibration mode map (or a frequency mode map). The vibration mode map may be used to avoid resonance (i.e., vibration amplification) by performing mapping such that an overlap between the natural frequency of the vehicle and the natural frequency of the human body does not occur.

The controller 130 may select a frequency capable of avoiding resonance between the vehicle and the human body as the appropriate frequency with reference the vibration mode map. The controller 130 may control seat vibration using a correlation between driver emotion modeling and sitting on the seat. Vibration of 1 Hz to 3 Hz in a forward and backward direction and human excitation of 5 Hz in forward and backward and in upward and downward directions may be described with a frequency where a possibility of resonance with a vehicle frequency is low by means of a human vibration-related frequency (i.e., a vibration mode map) to be considered in the development of the vehicle. This frequency may be selected as a frequency capable of avoiding resonance between the vehicle and the human body.

The controller 130 may determine an appropriate frequency of a back and thighs for vibration corresponding to the sleep state based on the weight of the user. The controller 130 may determine an appropriate frequency of a vibration signal using a correlation equation, such as Equation 1. Equation 1 is derived by analyzing human modeling-based big data according to the sitting state.

$$(f_b + f_f)^2 = k1 + \frac{k2}{m} \times a \qquad \text{Equation 1}$$

In Equation 1, k1 denotes the fixed variable preset by the system designer, k2 denotes the seat stiffness, m denotes the weight of the user, and a denotes the relative variable assigned with regard to the weight distribution of the back and the thighs on the seat through the analysis of the human modeling-based big data according to the sitting state. The relative variable may be applied to minimize distribution according to the sitting posture of the user and suitably set an emotional vibration frequency. The relative variable may be applied to avoid a corresponding frequency such that resonance with the natural frequency of a vehicle does not occur and set the emotional vibration frequency. Further, in Equation 1, $f_b$ denotes the seat back vibration excitation frequency (or the seat back vibration frequency) and $f_f$ denotes the seat frame vibration excitation frequency (or the seat cushion vibration frequency). The division of $f_b$ and $f_f$ may be determined according to the sitting posture of the user.

As an example, the controller 130 may determine an appropriate lateral frequency as 2 Hz based on a real weight of a passenger riding in the vehicle. The controller 120 may also determine an appropriate thigh upward frequency as 4 Hz to 7 Hz.

The controller 130 may select a vibration waveform (or a vibration type or a vibration pattern) based on the sleep state. Referring to FIG. 3, when the sleep state is determined as the sleep boundary stage, the controller 130 may determine a first vibration waveform. The first vibration waveform may be a patting pattern such as when putting a child to sleep and may help to sleep. The first vibration waveform may be implemented as sine wave excitation of 2 Hz on the back (HIGH) of the vehicle seat.

When the sleep state is determined as the sleep stage, the controller 130 may determine a second vibration waveform. The second vibration waveform may be implemented as a crossing wave of 2 Hz to 7 Hz, which may result in patting across the back and thighs. The crossing wave may be a waveform where a sine wave and a triangle wave cross with each other.

When the sleep state is determined as the deep sleep stage, the controller 130 may determine a third vibration waveform. The third vibration waveform may be implemented as a triangle wave of 4 Hz to 7 HZ on thighs (BASS) and may contribute to a deep sleep therapy by giving a sense of stability.

The controller 130 may analyze whether the back is close to the seat, surface pressure distribution, and a load balance based on frequency-acceleration for each seat portion detected by the detector 110 and may determine a sitting posture. The controller 130 may determine whether a body part (e.g., the back) of the user is close to the seat back based on frequency-acceleration in the seat back.

The controller 130 may analyze surface pressure distribution of the seat back and the lower frame, surface pressure distribution of the seat cushion, and/or the like and may determine a load balance (or a left and right balance and a front and rear balance) on the vehicle seat. The controller 130 may analyze whether the body part is close to the seat back based on frequency-acceleration in the seat back. The controller 130 may analyze a load balance based on frequency-acceleration in the seat cushion. The controller 130 may then determine (or estimate) a sitting posture (or a surface pressure distribution area). The controller 130 may correct a vibration excitation force in an X direction and a Z direction based on the sitting posture of the user.

As an example, the controller 130 may decrease a frequency amplitude of a portion where the vibration excitation force is high through pressure applied to the vehicle seat and may increase a frequency amplitude of a portion where the vibration excitation force is low. The controller 130 may thus be useful when differently giving back and thigh balances upon sleep vibration or deep sleep vibration excitation.

The controller 130 may generate seat vibration based on the determined vibration frequency and the determined vibration waveform. For example, the controller 130 may generate vibration having the corrected vibration excitation force.

The controller 130 may generate sleep therapy vibration and may monitor the sleep state of the user. For example, the controller 130 may continuously measure an EEG and a heart rate of the user by means of the detector 110. The controller 130 may recognize a change in the sleep state by means of a change in the EEG and the heart rate. The controller 130 may detect a change from a sleep stage to a deep sleep stage by means of the change in the EEG and the heart rate, for example.

The controller 130 may determine whether a predetermined threshold time has elapsed after the sleep state is changed. When it is identified that the threshold time has not elapsed, the controller 130 may maintain the generation of existing sleep therapy vibration. When it is determined that the threshold time has elapsed, the controller 130 may redetermine a vibration frequency and a vibration waveform. For example, when the threshold time elapses after the sleep state is changed, the controller 130 may redetermine a vibration frequency and a vibration waveform based on the changed sleep state. The controller 130 may then generate seat vibration based on the redetermined vibration frequency and the redetermined vibration waveform.

The controller 130 may monitor a state of the user using a camera (not shown) and may adjust a seat angle and a leg support. The controller 130 may monitor face motion and body motion of the user who is sleeping using the camera. When the face of the user is tilted to the front or side, the controller 130 may adjust an angle of the seat back to the rear. When the user tosses and turns, the controller 130 may adjust an angle of at least one of the vehicle seat, the leg support, or a combination thereof.

The controller 130 may measure interior noise using a noise measurement device and may operate a noise canceling function. As an example, the controller 130 may measure interior noise when the sleep pattern does move to the next stage although a certain time has elapsed, using feedback information. When the interior noise is greater than a threshold, the controller 130 may operate the noise canceling function without user input.

Figure 4:
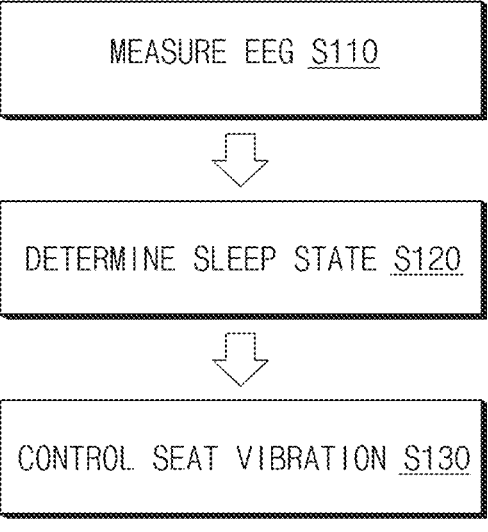
FIG. 4 is a flowchart illustrating a vehicle seat control method, according to embodiments of the present disclosure.

FIG. 4 is a flowchart illustrating a vehicle seat control method, according to embodiments of the present disclosure.

Referring to FIG. 4, in an operation S110, the controller 130 of the vehicle seat control apparatus 100 of FIG. 1 may measure an EEG of a user using the detector 110. As an example, the controller 130 may measure an EEG of the user by means of an EEG measurement device. The controller 130 may measure a heart rate of the user using an ECG measurement device.

In an operation S120, the controller 130 may analyze the measured EEG of the user and may determine a sleep state of the user. For example, the controller 130 may analyze a waveform of the EEG and may determine the sleep state of the user. When it is determined that the EEG of the user is a theta wave, the controller 130 may determine the sleep state as a sleep boundary stage. When it is determined that the EEG of the user is a delta wave, the controller 130 may determine the sleep state as a sleep stage. When it is determined that the EEG of the user is a beta wave, the controller 130 may determine the sleep state as a deep sleep stage. The controller 130 may analyze a heart rate in addition to the waveform of the EEG and may determine the sleep state of the user with regard to the analyzed result.

In an operation S130, the controller 130 may control seat vibration based on the determined sleep state. The controller 130 may control the driving device 120 of FIG. 1 to generate sleep therapy vibration corresponding to the sleep state. For example, the controller 130 may generate vibration having a sine wave when the sleep state is determined as the sleep boundary stage. The controller 130 may generate vibration having a crossing wave when the sleep state is determined as the sleep stage. When the sleep state is determined as the deep sleep stage, the controller 130 may generate vibration having a triangle wave.

Figure 5:
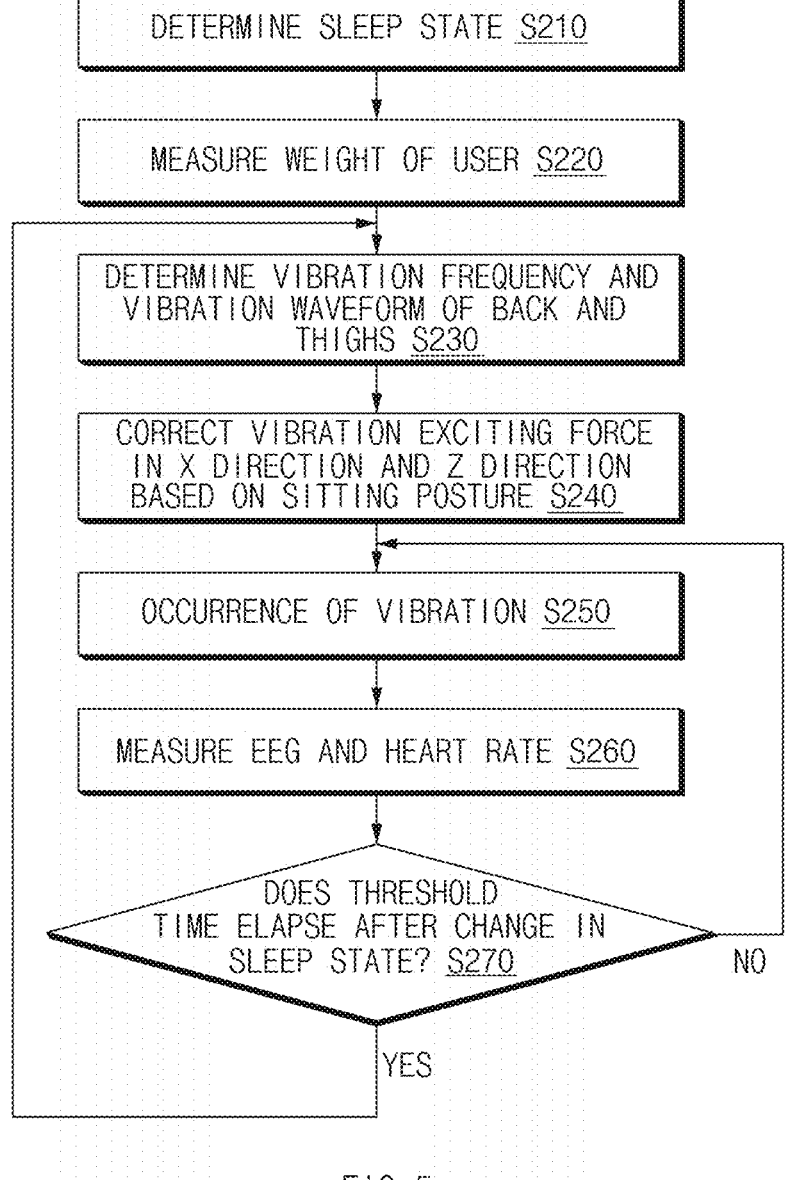
FIG. 5 is a flowchart illustrating a seat vibration control method, according to embodiments of the present disclosure.

FIG. 5 is a flowchart illustrating a seat vibration control method, according to embodiments of method present disclosure.

In an operation S210, the controller 130 of the vehicle seat control apparatus 100 of FIG. 1 may determine a sleep state. The controller 130 may monitor an EEG of a user riding in a vehicle and may determine a sleep state of the user. Furthermore, the controller 130 may determine a sleep state selected according to manipulation of a user interface of the user sitting on a vehicle seat as the sleep state of the user.

In an operation S220, the controller 130 may measure a weight of the user in the state where the sleep state is determined. The controller 130 may measure the weight of the user using a weight sensor embedded in the vehicle seat.

In an operation S230, the controller 130 may determine a vibration frequency and a vibration waveform of a back and thighs of the user based on the weight of the user. The controller 130 may determine a back vibration frequency, a back vibration waveform, a thigh vibration frequency, and a thigh vibration waveform with regard to weight distribution of the back and the thighs on the seat through an analysis of human modeling-based data (e.g., big data) according to a sitting posture. The controller 130 may determine a vibration waveform based on the sleep state.

In an operation S240, the controller 130 may correct a vibration excitation force in an X direction and a Z direction based on the sitting posture of the user. The controller 130 may analyze whether the back is close to the seat, surface pressure distribution, and a load balance based on frequency-acceleration for each seat portion detected by the detector 110 of FIG. 1 and may determine the sitting posture. The controller 130 may determine whether a body part (e.g., the back) of the user is close to a seat back based on frequency-acceleration in the seat back. The controller 130 may analyze surface pressure distribution of the seat back and a lower frame, surface pressure distribution of a seat cushion, and/or the like and may determine a load balance (or a left and right balance and a front and rear balance) on the vehicle seat. The controller 130 may analyze whether the body part is close to the seat back based on frequency-acceleration in the seat back and a load balance based on frequency-acceleration in the seat cushion and may determine (or estimate) a sitting posture (or a surface pressure distribution area). The controller 130 may correct a vibration excitation force in an X direction and a Z direction based on the sitting posture of the user.

In an operation S250, the controller 130 may generate seat vibration based on the determined vibration waveform and vibration waveform and the corrected vibration excitation force. The controller 130 may control the driving device 120 of FIG. 1 to generate sleep therapy seat vibration.

In an operation S260, the controller 130 may measure an EEG and a heart rate of the user. The controller 130 may monitor the EEG and the heart rate of the user using the detector 110.

In an operation S270, the controller 130 may determine whether a threshold time has elapsed after the sleep state is changed based on the EEG and the heart rate of the user. The controller 130 may determine whether there is a change in the sleep state of the user based on the change in the EEG and the heart rate of the user. The controller 130 may determine whether a predetermined threshold time has elapsed after the sleep state is changed. When it is determined that the threshold time has elapsed after the sleep state is changed, the controller 130 may repeat the operations S230-S270. On the other hand, when it is determined that the threshold time has not elapsed after the sleep state is changed, the controller 130 may maintain existing seat vibration.

Embodiments of the present disclosure may monitor a sleep state of a user using electroencephalogram (EEG) and may control seat vibration based on the sleep state, thus helping the user to sleep.

Furthermore, embodiments of the present disclosure may divide a sleep state into three stages and may control a seat vibration pattern through a customized frequency change for each divided stage, thus guiding the user to fall into a deep sleep.

Although the present disclosure has been described with reference to example embodiments and the accompanying drawings, the present disclosure is not limited thereto. The present disclosure may be variously modified and altered by those having ordinary skill in the art to which the present disclosure pertains without departing from the spirit and scope of the present disclosure claimed in the following claims. Therefore, embodiments of the present disclosure are provided for illustrative purpose and are not intended to limit the technical spirit of the present disclosure. The scope of the present disclosure should be construed on the basis of the following claims and all the technical ideas within the scope equivalent to the claims should be included in the scope of the present disclosure.

What is claimed is:

1. A vehicle seat control apparatus, comprising:
a detector configured to detect biometric information of a user;
a driving device configured to control a vibrator embedded in a vehicle seat; and
a controller connected with the detector and the driving device,
wherein the controller is configured to:
determine a sleep state of the user based on the biometric information detected by the detector, wherein the sleep state is divided into a sleep boundary stage, a sleep stage, and a deep sleep stage;
determine a frequency and a waveform of seat vibration based on the sleep state, wherein the controller is configured to
select the waveform of the seat vibration as a sine wave in response to determining that the sleep state is the sleep boundary stage, select the waveform of the seat vibration as a crossing wave in which a sine wave and a triangle wave cross with each other in response to determining that the sleep state is the sleep stage, and
select the waveform of the seat vibration as a triangle wave in response to determining that the sleep state is the deep sleep stage; and
generate the seat vibration by controlling the driving device based on the frequency and the waveform of the seat vibration.

2. The vehicle seat control apparatus of claim 1, wherein the detector includes:
an electroencephalogram (EEG) measurement device configured to measure an EEG of the user.

3. The vehicle seat control apparatus of claim 2, wherein the controller is configured to:
analyze the EEG of the user; and
determine the sleep state based on a result of analyzing the EEG.

4. The vehicle seat control apparatus of claim 1, wherein the controller is configured to select a frequency of the seat vibration based on the sleep state.

5. The vehicle seat control apparatus of claim 4, wherein the controller is configured to:
set a concept of correlation between sleep and frequency by analyzing vibration frequency distribution and a ratio of sleeping passengers;
set a vibration mode map capable of avoiding resonance between a natural frequency of a vehicle and a natural frequency of a human body based on the set concept; and
select a frequency capable of avoiding resonance between the vehicle and the human body as the frequency of the seat vibration with reference to the vibration mode map.

6. The vehicle seat control apparatus of claim 1, wherein the controller is configured to:
determine a frequency of the seat vibration, the frequency of the seat vibration corresponding to the sleep state, based on a weight of the user.

7. The vehicle seat control apparatus of claim 1, wherein the controller is configured to determine a seat back vibration frequency and a seat cushion vibration frequency with regard to weight distribution for each body part through an analysis of human modeling-based data according to a sitting state.

8. The vehicle seat control apparatus of claim 1, wherein the detector is configured to detect i) one or both of frequency of vibration or acceleration and ii) surface pressure for each seat portion using an accelerometer and a pressure sensor.

9. The vehicle seat control apparatus of claim 8, wherein the controller is configured to:
analyze whether a body part is close to the vehicle seat, surface pressure distribution, and a load balance based on the i) one or both of the frequency of vibration or the acceleration and ii) the surface pressure for each seat portion; and
determine a sitting posture of the user based on the analyzed result.

10. The vehicle seat control apparatus of claim 9, wherein the controller is configured to correct a vibration excitation force based on the sitting posture of the user.

11. The vehicle seat control apparatus of claim 10, wherein the controller is configured to:
decrease an amplitude of vibration at a portion of the vehicle seat where the vibration excitation force is determined to be relatively high compared to other portions of the vehicle seat based on a pressure applied to the vehicle seat; and increase an amplitude of vibration at a portion of the vehicle seat where the vibration excitation force is determined to be relatively low compared to other portions of the vehicle seat based on the pressure applied to the vehicle seat.

12. The vehicle seat control apparatus of claim 1, wherein the controller is configured to:

monitor the sleep state of the user based on the biometric information detected by the detector while generating the seat vibration; and recognize a change in the sleep state based on the result of monitoring the sleep state of the user.

13. The vehicle seat control apparatus of claim 12, wherein the controller is configured to:

redetermine a frequency and a waveform of the seat vibration in response to detecting that a predetermined threshold time has elapsed after the change in the sleep state is recognized.

14. The vehicle seat control apparatus of claim 1, wherein the controller is configured to:

monitor the sleep state of the user using a camera; and adjust an angle, relative to a floor of the vehicle, of at least one of the vehicle seat, a leg support, or a combination thereof, based on the result of monitoring the sleep state of the user.

15. The vehicle seat control apparatus of claim 1, wherein the controller is configured to:

measure interior noise of a vehicle using a noise measurement device; and control an operation of a noise canceling function based on the measured interior noise.

16. A vehicle seat control method, comprising:

detecting biometric information of a user using a detector;

determining a sleep state of the user based on the biometric information, wherein the sleep state is divided into a sleep boundary stage, a sleep stage, and a deep sleep stage;

determining a frequency and a waveform of seat vibration based on the sleep state, including selecting the waveform of the seat vibration as a sine wave in response to determining that the sleep state is the sleep boundary stage;

selecting the waveform of the seat vibration as a crossing wave in which a sine wave and a triangle wave cross with each other in response to determining that the sleep state is the sleep stage; and selecting the waveform of the seat vibration as a triangle wave in response to determining that the sleep state is the deep sleep stage; and generating the seat vibration by controlling a driving device based on the frequency and the waveform of the seat vibration.

17. The vehicle seat control method of claim 16, wherein detecting the biometric information of the user includes:

measuring an EEG of the user using an EEG measurement device.

18. The vehicle seat control method of claim 17, wherein determining the sleep state of the user includes:

analyzing the EEG of the user; and determining the sleep state based on a result of analyzing the EEG.

19. The vehicle seat control method of claim 16, wherein determining the frequency and the waveform of the seat vibration includes:

selecting a frequency of the seat vibration based on the sleep state.

20. The vehicle seat control method of claim 19, wherein selecting the frequency of the seat vibration includes:

setting a concept of correlation between sleep and frequency by analyzing vibration frequency distribution and a ratio of sleeping passengers;

setting a vibration mode map capable of avoiding resonance between a natural frequency of a vehicle and a natural frequency of a human body based on the set concept; and selecting a frequency capable of avoiding resonance between the vehicle and the human body as the frequency of the seat vibration with reference to the vibration mode map.

21. The vehicle seat control method of claim 16, wherein determining the frequency and the waveform of the seat vibration includes:

measuring a weight of the user; and determining a frequency of the seat vibration, the frequency of the seat vibration corresponding to the sleep state, based on the weight of the user.

22. The vehicle seat control method of claim 16, wherein determining the frequency and the waveform of the seat vibration includes:

determining a seat back vibration frequency and a seat cushion vibration frequency with regard to weight distribution for each body part through an analysis of human modeling-based big data according to a sitting state.

23. The vehicle seat control method of claim 16, further comprising:

determining a sitting posture of the user; and correcting a vibration excitation force based on the sitting posture.

24. The vehicle seat control method of claim 23, wherein determining the sitting posture of the user includes:

determining i) one or both of frequency of vibration or acceleration and ii) surface pressure for each seat portion using an accelerometer and a pressure sensor;

analyzing whether a body part is close to a vehicle seat, surface pressure distribution, and a load balance based on the i) one or both of the frequency of vibration or the acceleration and ii) the surface pressure for each seat portion; and determining the sitting posture based on the analyzed result.

25. The vehicle seat control method of claim 24, further comprising:

correcting a vibration excitation force based on the sitting posture of the user, after determining the sitting posture of the user.

26. The vehicle seat control method of claim 25, wherein correcting the vibration excitation force includes:

decreasing an amplitude of vibration at a portion of the vehicle seat where the vibration excitation force is determined to be relatively high compared to other portions of the vehicle seat based on a pressure applied to the vehicle seat; and increasing an amplitude of vibration at a portion of the vehicle seat where the vibration excitation force is determined to be relatively low compared to other portions of the vehicle seat based on the pressure applied to the vehicle seat.

27. The vehicle seat control method of claim 16, further comprising:

monitoring the sleep state of the user based on the biometric information detected by the detector while generating the seat vibration;

recognizing a change in the sleep state based on the result of monitoring the sleep state of the user; and redetermining a frequency and a waveform of the seat vibration in response to detecting that a predetermined threshold time elapses after the change in the sleep state is recognized.

28. The vehicle seat control method of claim 16, further comprising:

monitoring the sleep state of the user using a camera; and adjusting an angle, relative to a floor of the vehicle, of at least one of a vehicle seat, a leg support, or a combination thereof based on the result of monitoring the sleep state of the user.

29. The vehicle seat control method of claim 16, further comprising:

measuring interior noise of a vehicle using a noise measurement device; and controlling an operation of a noise canceling function based on the measured interior noise.

\* \* \* \* \*